United States Patent
Keating et al.

(10) Patent No.: US 9,384,580 B2
(45) Date of Patent: Jul. 5, 2016

(54) MULTIPLE IMAGE GENERATION FROM A SINGLE PATIENT SCAN

(71) Applicant: Dental Imaging Technologies Corporation, Hatfield, PA (US)

(72) Inventors: Robert Keating, Chalfont, PA (US); Michael Parma, Chalfont, PA (US); Richard H. Elvin, Quakertown, PA (US); Edward S. Walsh, Media, PA (US); Douglas Tenney, Audubon, PA (US); Michael S. O'Donnell, Macungle, PA (US); George Cocco, Havertown, PA (US)

(73) Assignee: DENTAL IMAGING TECHNOLOGIES CORPORATION, Hatfield, PA (US)

( * ) Notice: Subject to any disclaimer, the term of this patent is extended or adjusted under 35 U.S.C. 154(b) by 181 days.

(21) Appl. No.: 13/766,585

(22) Filed: Feb. 13, 2013

(65) Prior Publication Data

US 2014/0226885 A1     Aug. 14, 2014

(51) Int. Cl.
*G06K 9/00* (2006.01)
*G06T 15/00* (2011.01)
*A61B 6/03* (2006.01)
(Continued)

(52) U.S. Cl.
CPC ............ *G06T 15/00* (2013.01); *A61B 6/032* (2013.01); *A61B 6/14* (2013.01); *A61B 6/4085* (2013.01); *A61B 6/5205* (2013.01); *A61B 6/5223* (2013.01); *A61B 6/563* (2013.01); *G06K 9/00362* (2013.01)

(58) Field of Classification Search
None
See application file for complete search history.

(56) References Cited

U.S. PATENT DOCUMENTS 5,338,198 A * 8/1994 Wu ............... A61C 13/0004
                                                    433/213
5,885,078 A * 3/1999 Cagna ............ A61C 8/0048
                                                    433/172

(Continued)

FOREIGN PATENT DOCUMENTS

CN    102014787 A    4/2011
CN    102573644 A    7/2012

(Continued)

OTHER PUBLICATIONS

EP14154388.4 Extended European Search Report dated Jun. 3, 2014 (7 pages).

(Continued)

*Primary Examiner* — Nancy Bitar
(74) *Attorney, Agent, or Firm* — Michael Best & Friedrich LLP

(57) ABSTRACT

Methods and systems for generating images. One system includes a processor. The processor is configured to receive image generation settings, receive projection data generated by a CT scan of an object, and automatically generate a first three-dimensional data set based on the projection data, wherein the first three-dimensional data set has a first field-of-view of the object. The processor is also configured to automatically generate a second three-dimensional data set based on the projection data and the image generation settings. The second three-dimensional data set has a second field-of-view of the object smaller than the first field-of-view in at least one dimension. In one embodiment, the second three-dimensional data set is transmitted to a service provider over at least one network.

19 Claims, 10 Drawing Sheets
(8 of 10 Drawing Sheet(s) Filed in Color)

(51) Int. Cl.
*A61B 6/14* (2006.01)
*A61B 6/00* (2006.01)

(56) References Cited

U.S. PATENT DOCUMENTS

| | | | | |
|---|---|---|---|---|
| 6,424,692 | B1* | 7/2002 | Suzuki | 378/4 |
| 6,970,585 | B1* | 11/2005 | Dafni | A61B 6/032 |
| | | | | 128/922 |
| 6,985,612 | B2* | 1/2006 | Hahn | 382/128 |
| 7,983,462 | B2 | 7/2011 | Sauer et al. | |
| 8,081,809 | B2 | 12/2011 | Dutta et al. | |
| 8,325,874 | B2* | 12/2012 | Shi et al. | 378/38 |
| 8,932,058 | B2* | 1/2015 | Fisker | A61C 9/00 |
| | | | | 433/173 |
| 9,116,217 | B2* | 8/2015 | Kim | G01R 33/4833 |
| 2004/0184643 | A1* | 9/2004 | Stantchev et al. | 382/128 |
| 2005/0105678 | A1 | 5/2005 | Nakashima | |
| 2006/0061570 | A1* | 3/2006 | Cheryauka | G06T 11/006 |
| | | | | 345/424 |
| 2007/0036418 | A1* | 2/2007 | Pan et al. | 382/131 |
| 2008/0037712 | A1* | 2/2008 | Klingenbeck-Regn | 378/167 |
| 2008/0075225 | A1* | 3/2008 | Kalender | 378/20 |
| 2008/0226150 | A1 | 9/2008 | Sadakane | |
| 2009/0175562 | A1* | 7/2009 | Pan et al. | 382/312 |
| 2010/0323329 | A1 | 12/2010 | Adusumilli et al. | |
| 2011/0109630 | A1* | 5/2011 | Breuer et al. | 345/424 |
| 2012/0189092 | A1* | 7/2012 | Jerebko et al. | 378/4 |
| 2012/0275675 | A1 | 11/2012 | Piron et al. | |
| 2014/0270440 | A1* | 9/2014 | Inglese et al. | 382/131 |

FOREIGN PATENT DOCUMENTS

| | | |
|---|---|---|
| DE | 102011003137 | 7/2012 |
| EP | 1973075 | 9/2008 |
| JP | 2006-087921 | 4/2006 |
| JP | 2009517144 A | 4/2009 |
| JP | 2011-512897 | 4/2011 |
| JP | 2013-500897 | 1/2013 |
| WO | 2011/014786 | 2/2011 |

OTHER PUBLICATIONS

Office Action received in Japanese Patent Application No. 2014-018391, dated Jan. 6, 2015 (8 pages).
Notice of Preliminary Rejection received in Korean Patent Application No. 10-2014-14999, dated Feb. 27, 2015 (11 pages).
1st Office Action from the State Intellectual Property Office of the People's Republic of China for Application No. 201410050314.2 dated Aug. 25, 2015 (9 pages).
Office Action from the Japanese Patent Office for Application No. 2014-018391 dated Aug. 25, 2015 (3 pages).
Office Action from the Korean Patent Office for Application No. 10-2014-0014999 dated Aug. 31, 2015.

* cited by examiner

MULTIPLE IMAGE GENERATION FROM A SINGLE PATIENT SCAN

FIELD

Embodiments of the invention relate to medical imaging systems, such as dental imaging systems. In particular, embodiments of the invention relate to systems and methods for automatically generating multiple images from a single scan of a patient.

BACKGROUND

Conventional cone beam computed tomography ("CBCT") dental imaging systems generate three-dimensional data of a patient. The three-dimensional, volumetric data can be used for different purposes. For example, doctors, dentists, and related clinicians typically require three-dimensional data having a full field-of-view but a low (i.e., coarse) resolution to provide images quickly for patient treatment or planning. In contrast, service providers, such as device or appliance manufacturers (e.g., dental or orthodontic device manufacturers) and companies providing custom treatment plans, often require three-dimensional data having a partial field of view but a higher (i.e., finer) resolution that can be automatically processed to design appliances or create custom treatment plans.

SUMMARY

Even though it would be useful to provide two different types of three-dimensional data, most commercially-available CBCT imaging systems perform a single scan of a patient and perform a single reconstruction to create volumetric data for use by a clinician in patient treatment and planning. If one or more separate three-dimensional data sets are required for an external service provider, the operator must manually initiate reconstruction of the separate data sets. Manually initiating the additional reconstructions requires operator time and introduces the potential for errors.

Embodiments of the present invention provide methods and systems for automatically reconstructing a second three-dimensional, volumetric data set from projection data captured during a computed tomography ("CT") scan of an object, such as a patient's head. The system can be configured to automatically transmit the second three-dimensional, volumetric data set to a service provider, e.g., an orthodontic device manufacturer. Preferably, the second three-dimensional, volumetric data set has characteristics suitable for automatic processing.

One embodiment provides a system for generating images. The system includes a processor. The processor is configured to receive image generation settings, receive projection data (a set of x-ray projection frames, plus the positions of the x-ray source and x-ray detector for each projection frame) generated by a CT scan of an object, generate a first three-dimensional, volumetric data set having a first field-of-view of the object from the projection data, and automatically generate a first image based on the first three-dimensional, volumetric data set. The processor is also configured to automatically generate a second three-dimensional, volumetric data set from the projection data and the image generation settings, wherein the second three-dimensional, volumetric data set has a second field-of-view of the object smaller than the first field-of-view in at least one dimension, and transmit the second three-dimensional, volumetric data set to a service provider over at least one network. Optionally, the second three-dimensional, volumetric data set can be generated and sent to the service provider without generating or displaying to an operator an image based on the second three-dimensional, volumetric data set. Alternatively, a second image can be generated based on the second three-dimensional, volumetric data set and displayed to the operator.

Another embodiment provides a method of generating images. The method includes: receiving, at a processor, image generation settings from an operator, initiating, at the processor, a scan of an object with a CT imaging apparatus based on the image generation settings; receiving, at the processor, projection data from the CT imaging apparatus acquired during the scan; and generating, at the processor, a first three-dimensional, volumetric data set from the projection data, wherein the first three-dimensional, volumetric data set has a first field-of-view of the object. The method also includes automatically, at the processor, generating a first image of the object based on the first three-dimensional, volumetric data set, and generating a signal to display the first image to the operator. In addition, the method includes automatically, at the processor, generating a second three-dimensional, volumetric data set based on the projection data and the image generation settings, the second three-dimensional, volumetric data set having a second field-of-view smaller than the first field-of-view in at least one dimension, and transmitting the second three-dimensional, volumetric data set to a device manufacturer over at least one network. Optionally, the second three-dimensional, volumetric data set can be generated and sent to the service provider without generating or displaying to an operator an image based on the second three-dimensional, volumetric data set. Alternatively, a second image can be generated based on the second three-dimensional, volumetric data set and displayed to the operator.

Yet another embodiment provides a system for generating images. The system includes: an imaging apparatus configured to scan an object and generate projection data; and a processor. The processor is configured to receive image generation settings, initiate a scan of the object with the imaging apparatus based on the image generation settings, receive from the imaging apparatus projection data generated during the scan, generate a first three-dimensional, volumetric data set from the projection data having a first field-of-view of the object, automatically generate from the first three-dimensional, volumetric data set a first image, and generate a signal to display the first image to an operator. The processor is also configured to automatically generate a second three-dimensional, volumetric data set from the projection data and the image generation settings while the first image is displayed to the operator, wherein the second three-dimensional, volumetric data set has a second field-of-view of the object smaller than the first field-of-view in at least one dimension. In addition, the processor is configured to automatically transmit the second three-dimensional, volumetric data set to a remote server operated by a dental appliance manufacturer over at least one network, optionally without displaying an image generated from the second three-dimensional, volumetric data set to the operator. The remote server automatically processes the second three-dimensional, volumetric data set to manufacture at least one dental appliance.

Other aspects of the invention will become apparent by consideration of the detailed description and accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
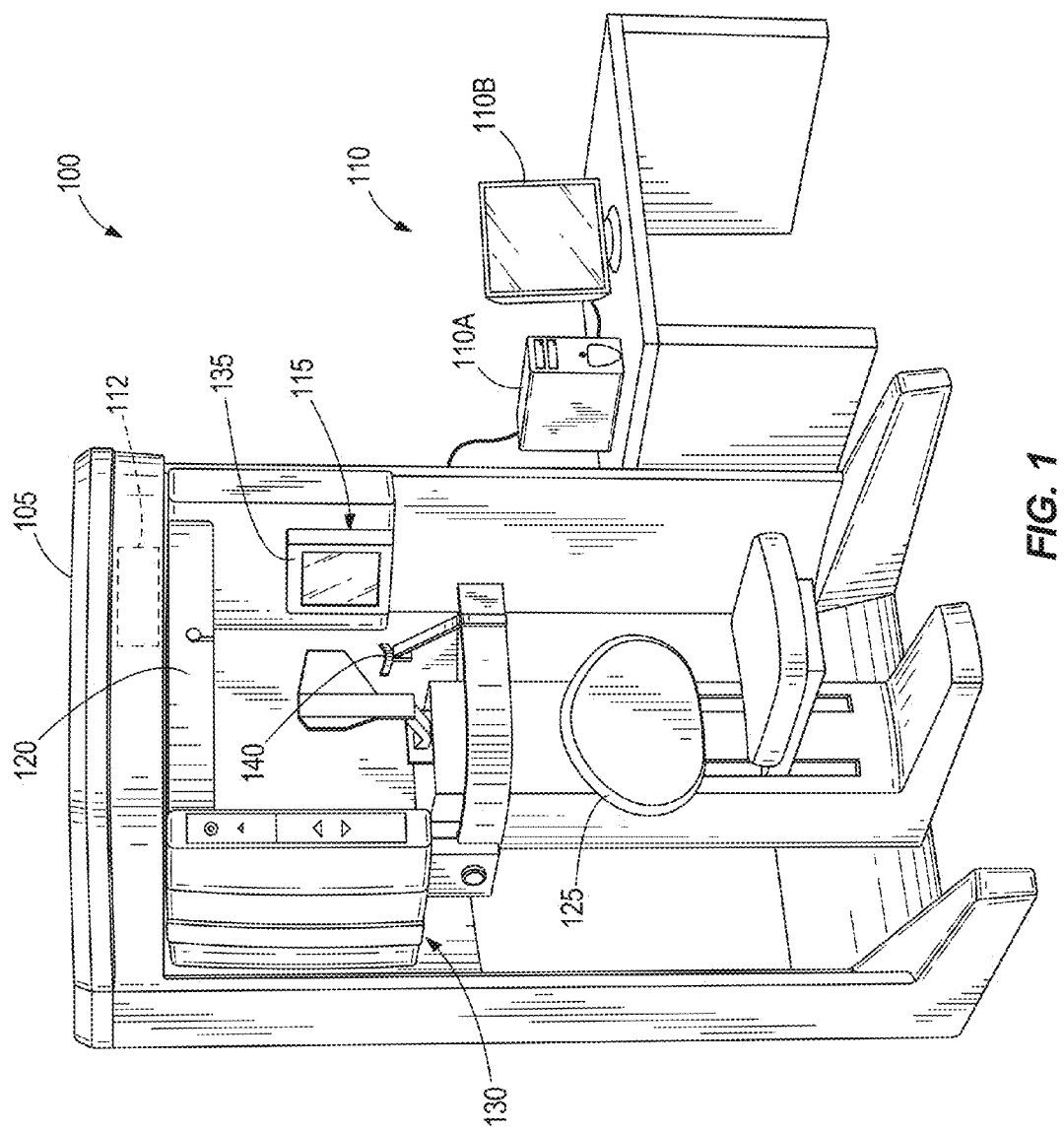
FIG. 1 illustrates a medical imaging system.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect. Also, electronic communications and notifications may be performed using any known means including direct connections, wireless connections, etc.

It should be noted that a plurality of hardware and software based devices, as well as a plurality of different structural components may be utilized to implement the invention. Furthermore, and as described in subsequent paragraphs, the specific configurations illustrated in the drawings are intended to exemplify embodiments of the invention and that other alternative configurations are possible.

FIG. 1 illustrates a medical imaging system 100. The system 100 includes an imaging apparatus 105 and a workstation 110. The imaging apparatus 105 includes a computed tomography ("CT") scanner that scans an object. The workstation 110 includes a computer 110A and a display, e.g., a touchscreen 110B. In some embodiments, the computer 110A and the touchscreen 110B are combined in a single device. Also, in some embodiments, the workstation 110 includes peripheral devices, such as a keyboard, mouse, printer, etc., connected to the computer 110A and/or the touchscreen 110B. In addition, it should be understood that in some embodiments, a non-touch-sensitive screen is used in place of or in addition to the touchscreen 110B.

As described in more detail below with respect to FIG. 2, the computer 110A is configured to receive projection data generated by the imaging apparatus 105, generate one or more sets of three-dimensional, volumetric data from the projection data, construct multiple images based on at least one of the sets of three-dimensional, volumetric data, display at least one of the generated images on the touchscreen 110B, and transmit at least one of the sets of three-dimensional, volumetric data to a service provider. In some embodiments, the computer 110A is also configured to control operation of the imaging apparatus 105 (e.g., based on user input or commands). The computer 110A can be connected to the imaging apparatus 105 by one or more wired or wireless connections.

The imaging apparatus 105 is, for example, a dental CT device and includes an on-board computer or processor 112, a radiation detector 115, a gantry 120, a support 125 for an object or patient being imaged, and a radiation source 130. The radiation detector 115 is positioned on the gantry 120 opposite the radiation source 130 and includes a detector array 135 having a plurality of detection elements. During a scan, a patient either sits on the support 125 or stands (and places his or her chin in a chin support 140). However, the invention is not limited to systems designed to accommodate seated or standing patients. For example, in some embodiments, the patient can lie down. The gantry 120 is rotated around the patient's head, and, as the gantry 120 rotates, the radiation source 130 moves and directs radiation at the patient's head at various angles. The radiation detector 115 detects the radiation passing through the patient and generates a set of projection frames, which are sent to the on-board computer or processor 112 within the imaging apparatus 105. The on-board computer or processor 112 receives the raw projection frames, and also keeps track of the positions of the radiation source 130 and the detector 115. During or after the scan, the on-board computer or processor 112 sends projection data, which comprises the projection frames and the positions of the radiation source 130 and the detector 115, to the workstation computer 110A.

Figure 2:
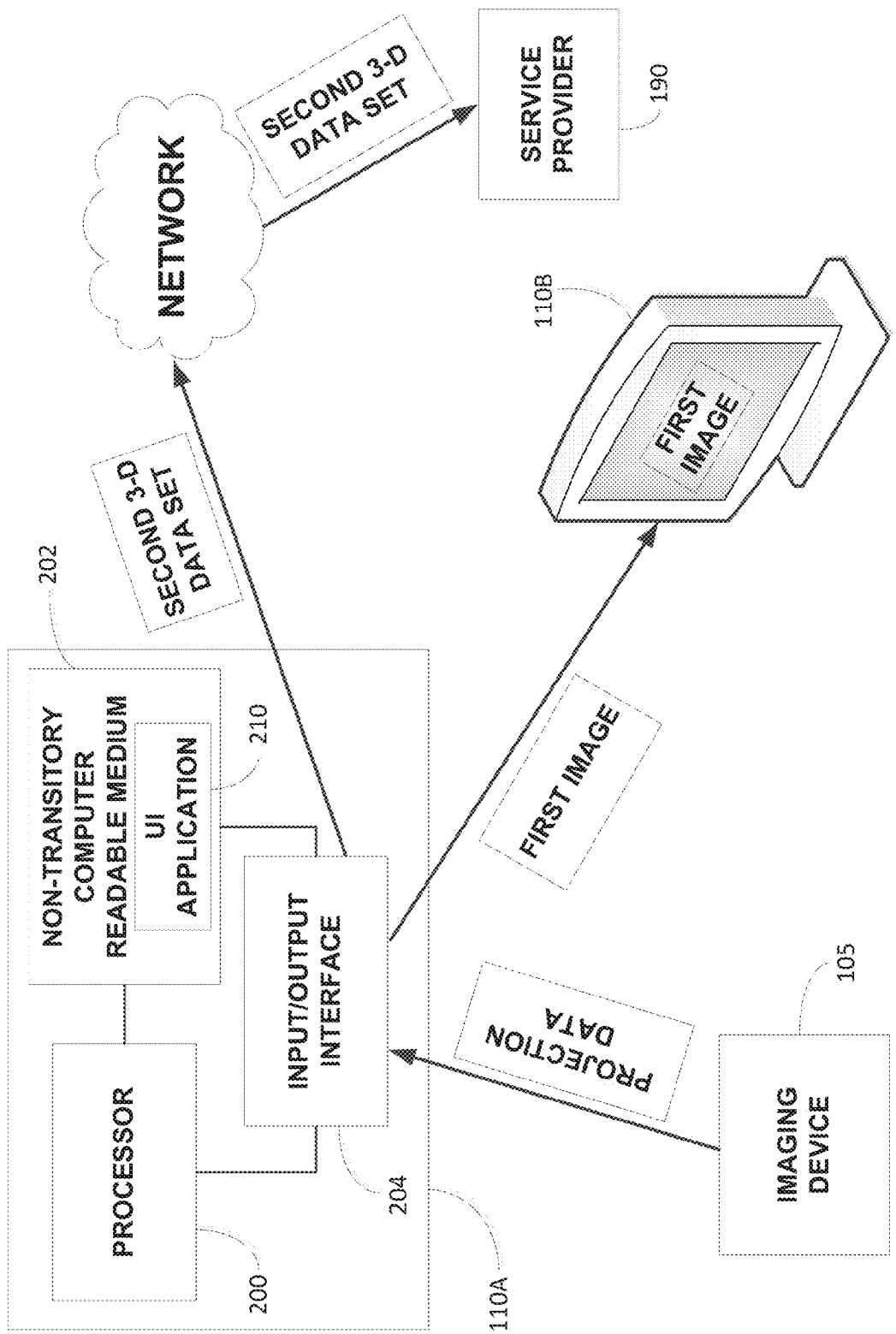
FIG. 2 schematically illustrates the medical imaging system of FIG. 1.

As illustrated in FIG. 2, the computer 110A is connected to the imaging apparatus 105, the touchscreen 110B, and a remote server 190 hosted by a service provider. The computer 110A includes a processor 200, non-transitory computer-readable medium 202, and an input/output interface 204. It should be understood that in other constructions, the computer 110A includes additional, fewer, or different components. The processor 200 is configured to retrieve instructions and data from the media 202 and execute, among other things, the instructions to receive projection data from the imaging apparatus 105, generate one or more sets of three-dimensional, volumetric data from the projection data, output data to the touchscreen 110B (i.e., generate a signal for displaying data on the touchscreen 110B), and output data to the server 190.

The input/output interface 204 transmits data from the processor 200 to external systems, networks, and/or devices and receives data from external systems, networks, and/or devices. In particular, the input/output interface 204 communicates with the imaging apparatus 105, the touchscreen 110B, and the server 190 over one or more wired or wireless connections and/or networks. The input/output interface 204 can also store data received from external sources to the media 202 and/or provide the data to the processor 200.

The computer-readable media 202 stores program instructions and data including a user interface ("UI") application (or "application") 210. When executed by the processor 200, the UI application 210 receives user commands, acquires data from the imaging apparatus 105, displays images and other information to a user on the touchscreen 110B, and transmits images to the server 190.

As illustrated in FIG. 2, the server 190 can be connected to the computer 110A by a network, e.g. as the Internet, a wide-area-network ("WAN"), a local-area-network ("LAN"), or combinations thereof. The server 190 is operated by a service provider and executes instructions for receiving three-dimensional, volumetric data or images from the computer 110A. In some embodiments, the server 190 also executes instructions for automatically-processing three-dimensional, volumetric data or images received from the computer 110A to generate various outputs. For example, as used in the present document, the phrase "service provider" includes any entity that provides devices or services in support of a clinician treating or planning treatment for a user. For example, a service provider can generate customized treatment plans for a clinician. A service provider can also generate device plans or actual devices for a patient. The devices can include dental appliances, such as retainers, bridges, braces, implants, and other orthodontic devices.

Figure 3:
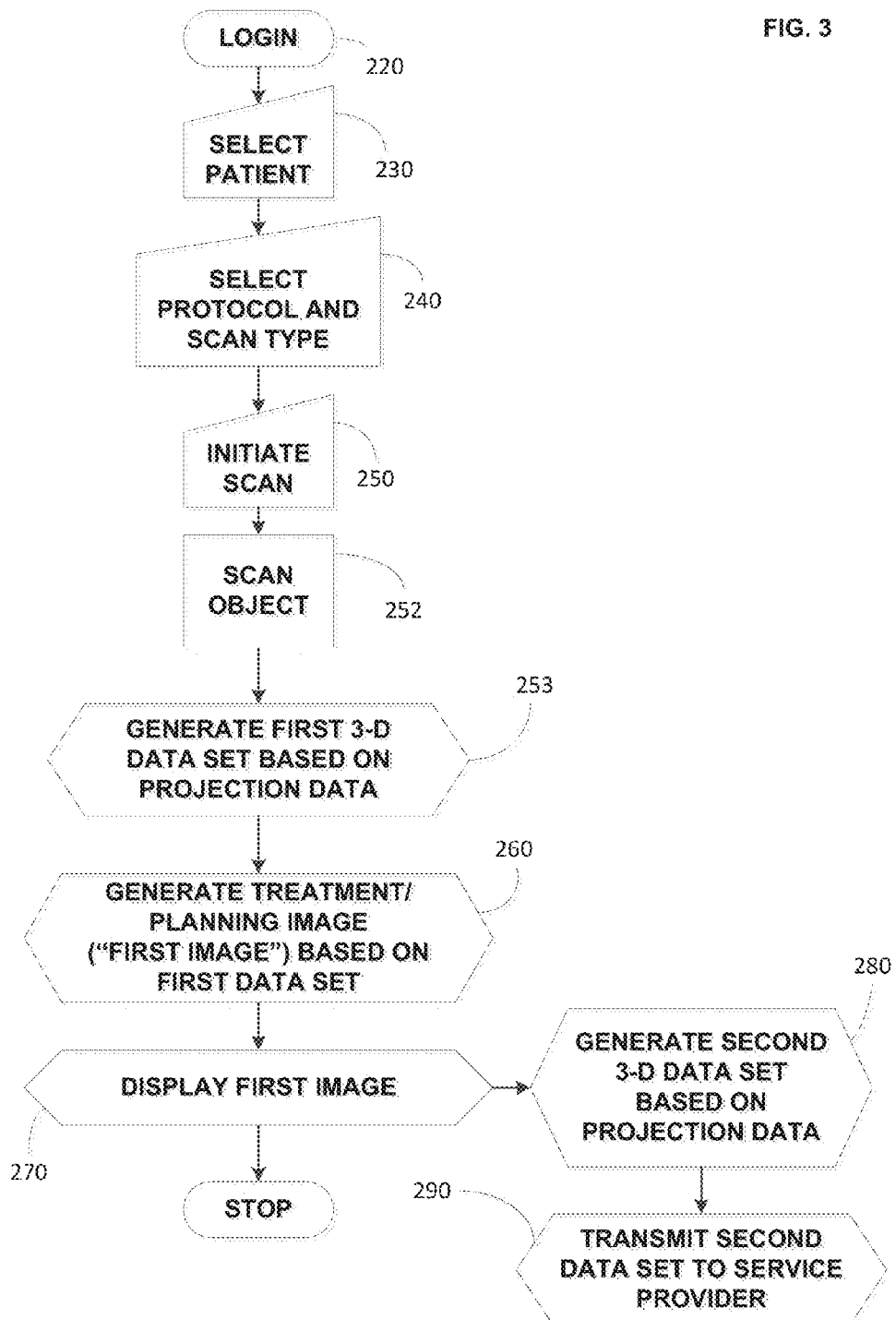
FIG. 3 is a flow chart illustrating a method of automatically generating multiple images from a single CT scan performed by the medical imaging system of FIG. 1.
Figure 4:
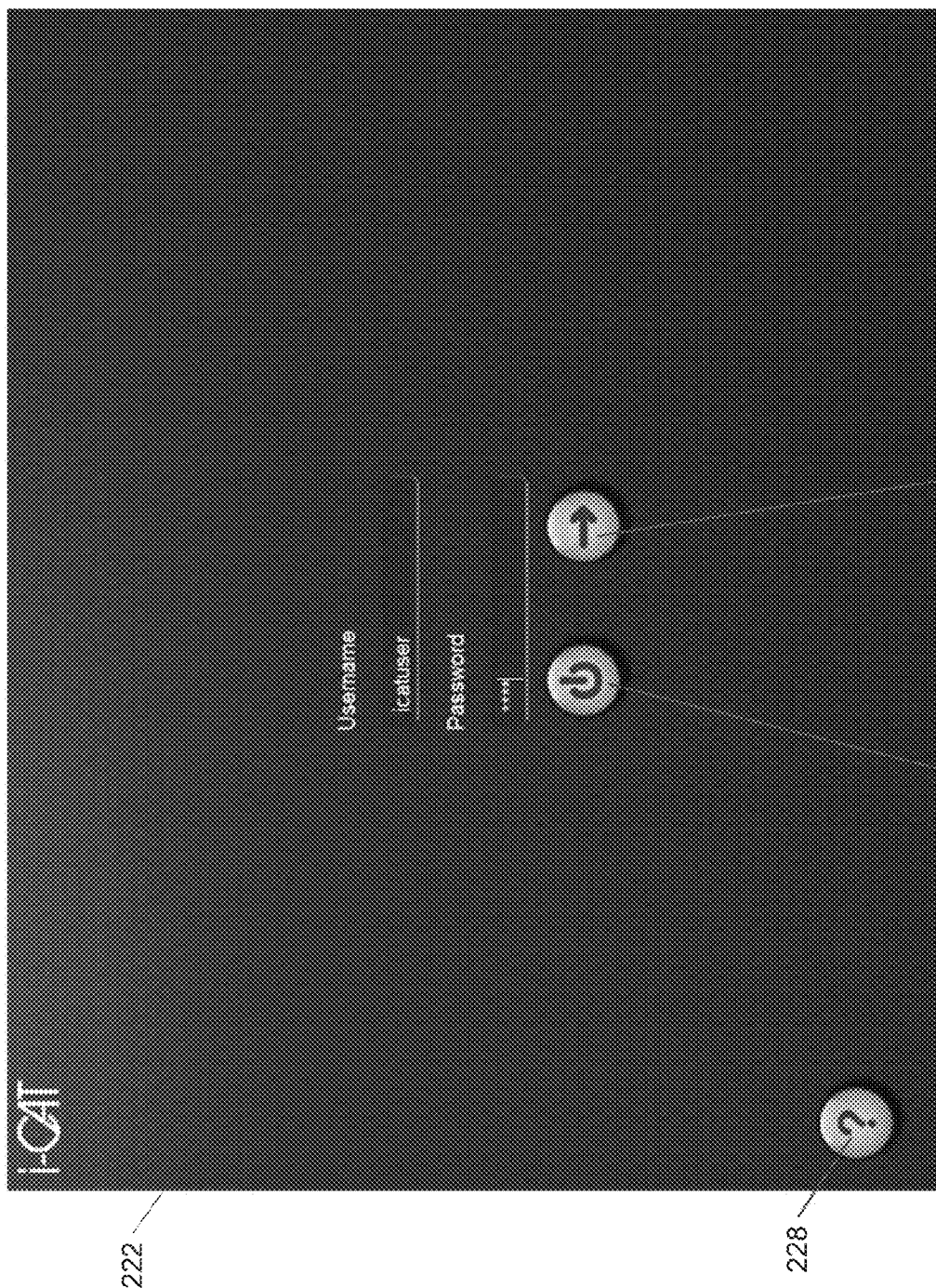
FIG. 4 illustrates a login screen.

A user uses the system 100 to initiate a CT scan. In particular, the processor 200 included in the computer 110A executes the user interface application 210 to display various screens to a user on the touchscreen 110B. A user enters commands and image generation settings through the displayed screens using buttons on the screens (selectable through the touchscreen 110B itself or separate peripheral devices, such as a keyboard or a mouse) to initiate a scan and inspect the data acquired during the scan. As illustrated in FIG. 3, to start the process, a user logs into the user application 210 (at step 220). For example, FIG. 4 illustrates a login screen 222 generated and displayed by the application 210. The login screen 222 prompts the user for a username and password and includes a next or enter button 224. In some embodiments, the login screen 222 also includes a power-off button 226 and a help button 228.

It is to be noted that, although the foregoing description refers to a user controlling the medical imaging system 100 through computer 110A, the system 100 can also include its own on-board user interface to allow the user to control the system 100 directly. Control through the on-board user interface can be instead of, or in addition to, control through computer 110A.

Figure 5:
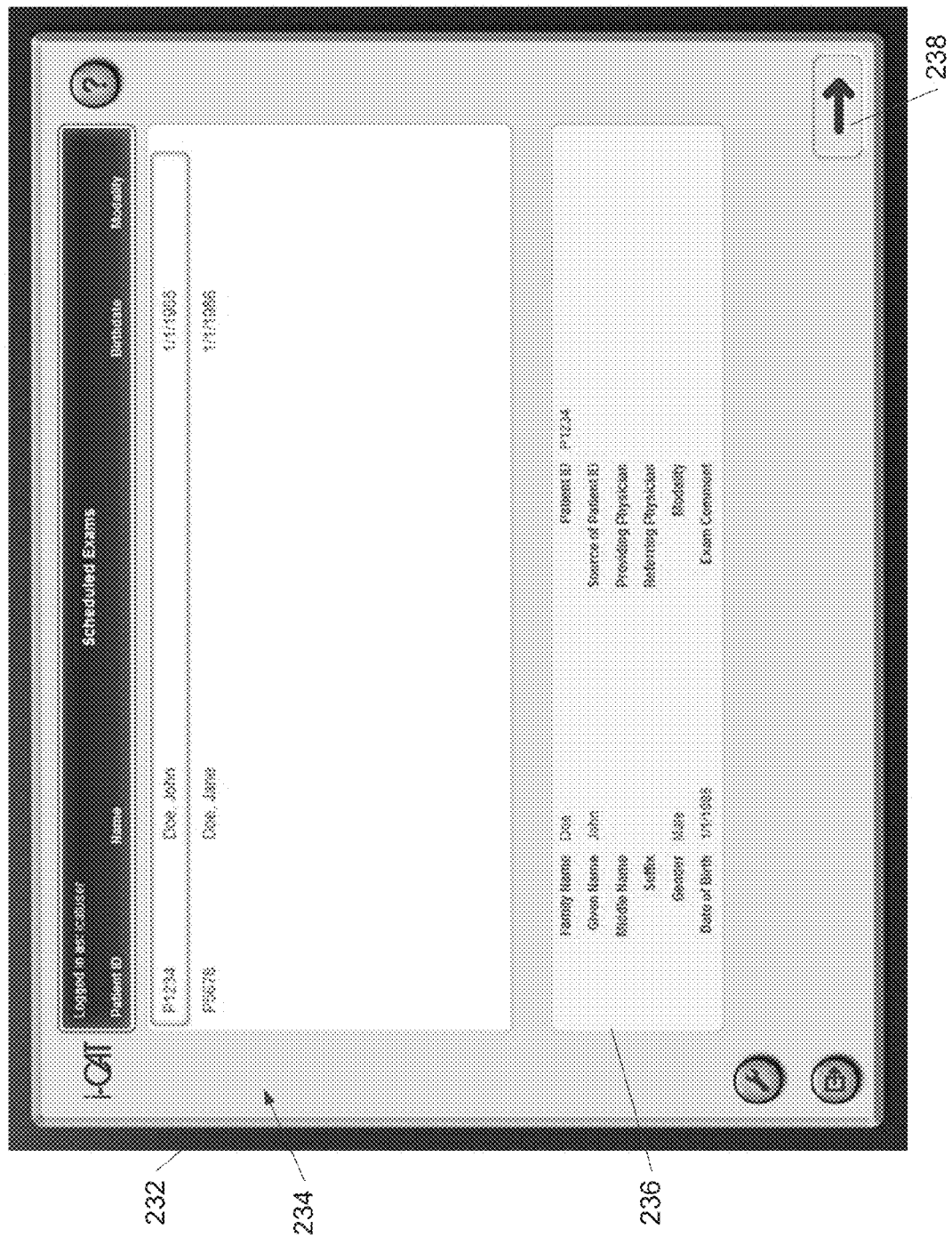
FIG. 5 illustrates a select-patient screen.

After the user logs in, the user selects a patient (at step 230). For example, FIG. 5 illustrates a select-patient screen 232 generated and displayed by the application 210. The screen 232 includes a list 234 of scheduled scans or exams. In some embodiments, the scheduled scans or exams are provided by a separate system or device, such as a picture archiving and communication system ("PACS") or a patient management system. As illustrated in FIG. 5, the screen 232 also includes a detail section 236 that provides additional data regarding a particular patient included in the list 234. After selecting a patient from the list 234 (e.g., by clicking on a listed patient), the user can select a next button 238.

Figure 6:
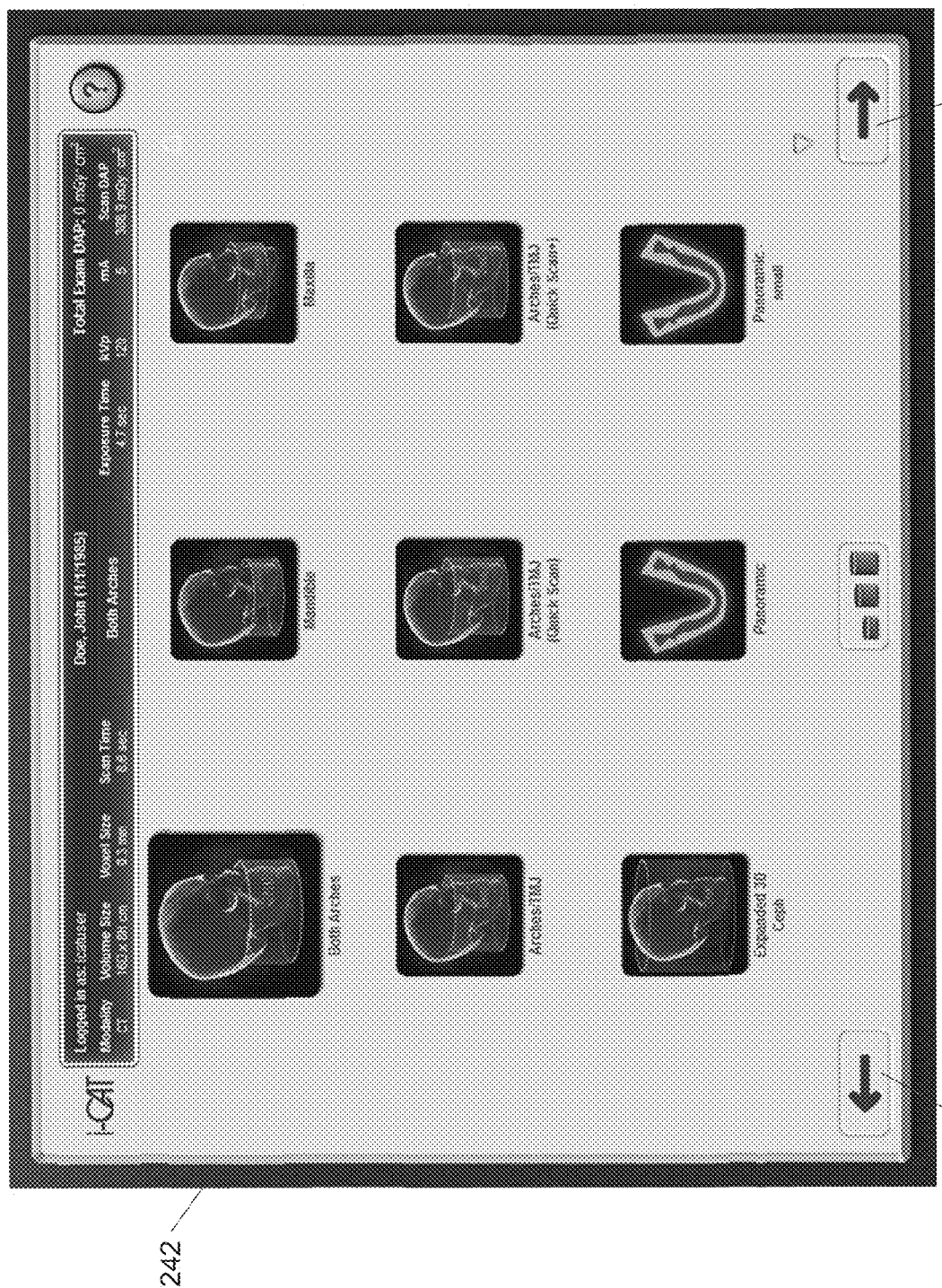
FIG. 6 illustrates a select-protocol screen.
Figure 7:
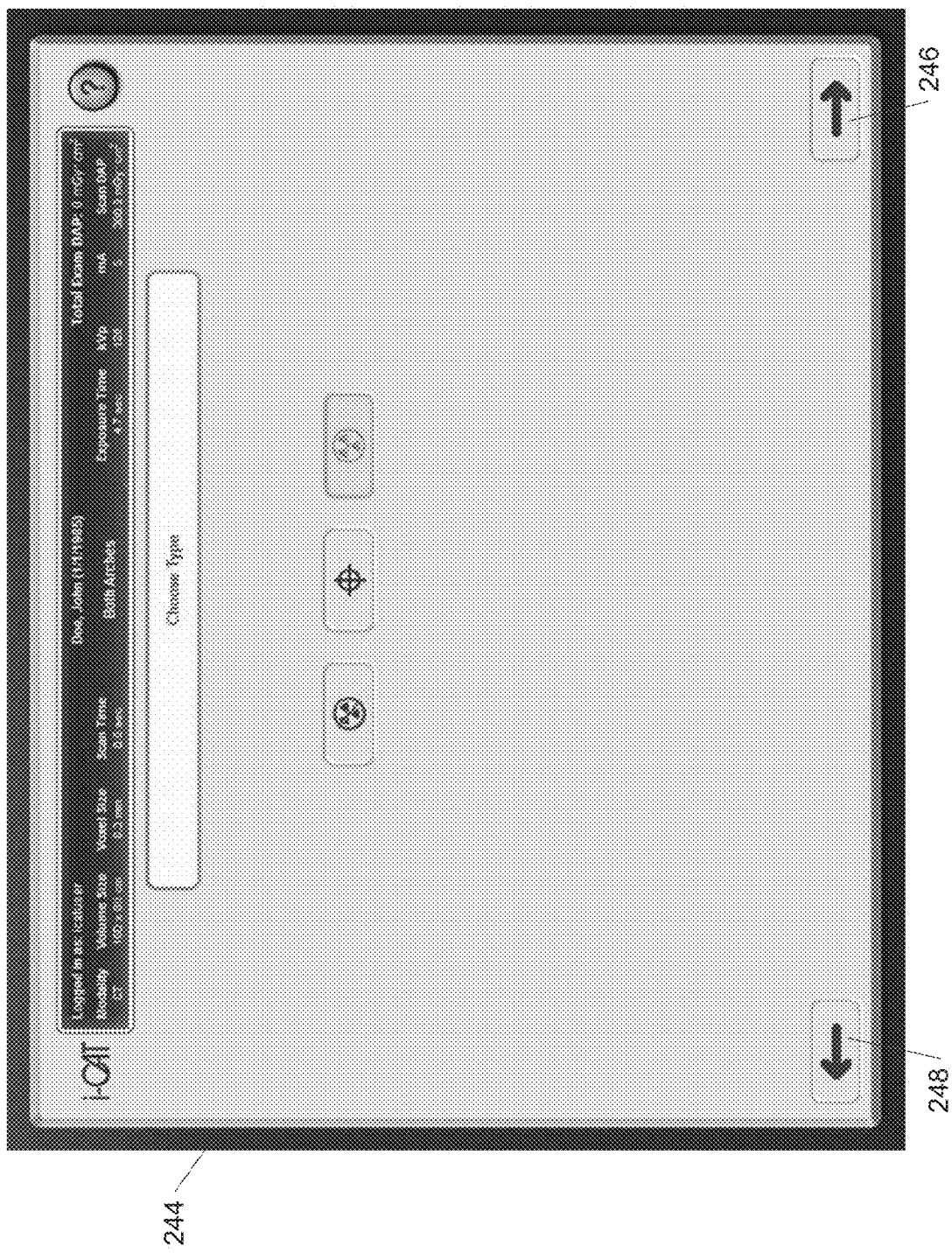
FIG. 7 illustrates a select-scan-type screen.

The user also selects image generation settings. For example, a user can select a scan protocol and a scan type (at step 240). FIG. 6 illustrates a select-protocol screen 242 generated and displayed by the application 210, and FIG. 7 illustrates a select-scan-type screen 244 generated and displayed by the application 210. The screens 242 and 244 include a next button 246 that the user can select after making a selection on a particular screen. In addition, the screens 242 and 244 include a back button 248 that the user can select to return to a previously-displayed screen. In some embodiments, one or more of the scan protocols included in the select-protocol screen 242 includes image generation settings pre-defined for a particular type of scan. As described below in more detail, the image generation settings are used to automatically generate three-dimensional, volumetric data or images for a service provider. In some embodiments, one or more of the scan protocols and/or the associated image generation settings are pre-selected by a user and set as "favorites" for the user. Therefore, when the user logs into the application 210, the application 210 includes the user's predefined "favorites" on the select-protocol screen 242.

Figure 8:
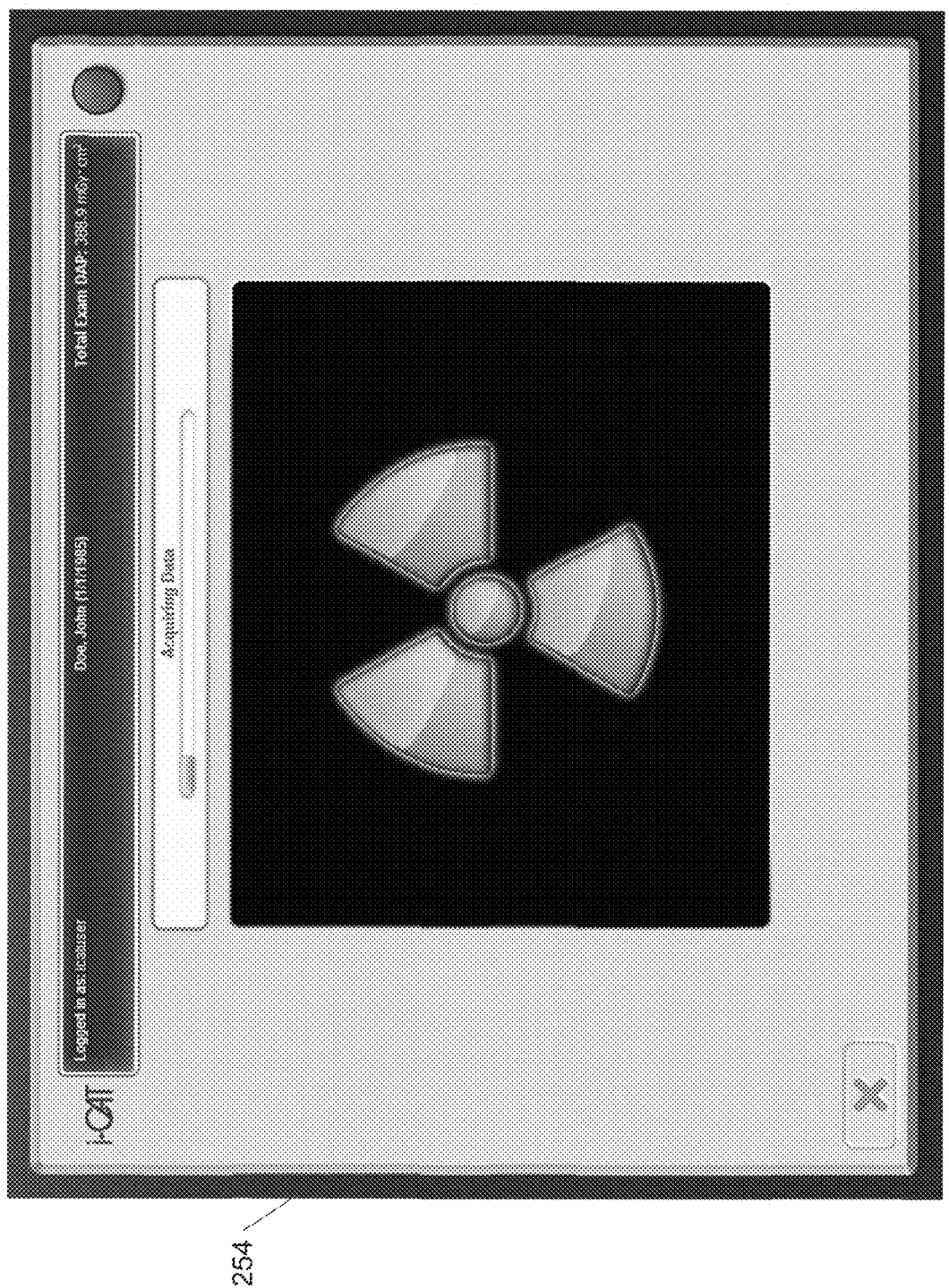
FIG. 8 illustrates an acquiring-data screen.

After the user selects the patient, scan protocol, and scan type, the user initiates the scan (e.g., by selecting the next button 246 on the select-scan-type screen 244) (at step 250). To start the scan, the application 210 communicates with the imaging apparatus 105 to initiate a scan as specified by the user (at step 252). In some embodiments, the application 210 displays an acquiring-image screen 254, as illustrated in FIG. 8, while the scan is performed and the application 210 acquires the projection data from the imaging apparatus 105.

Figure 9:
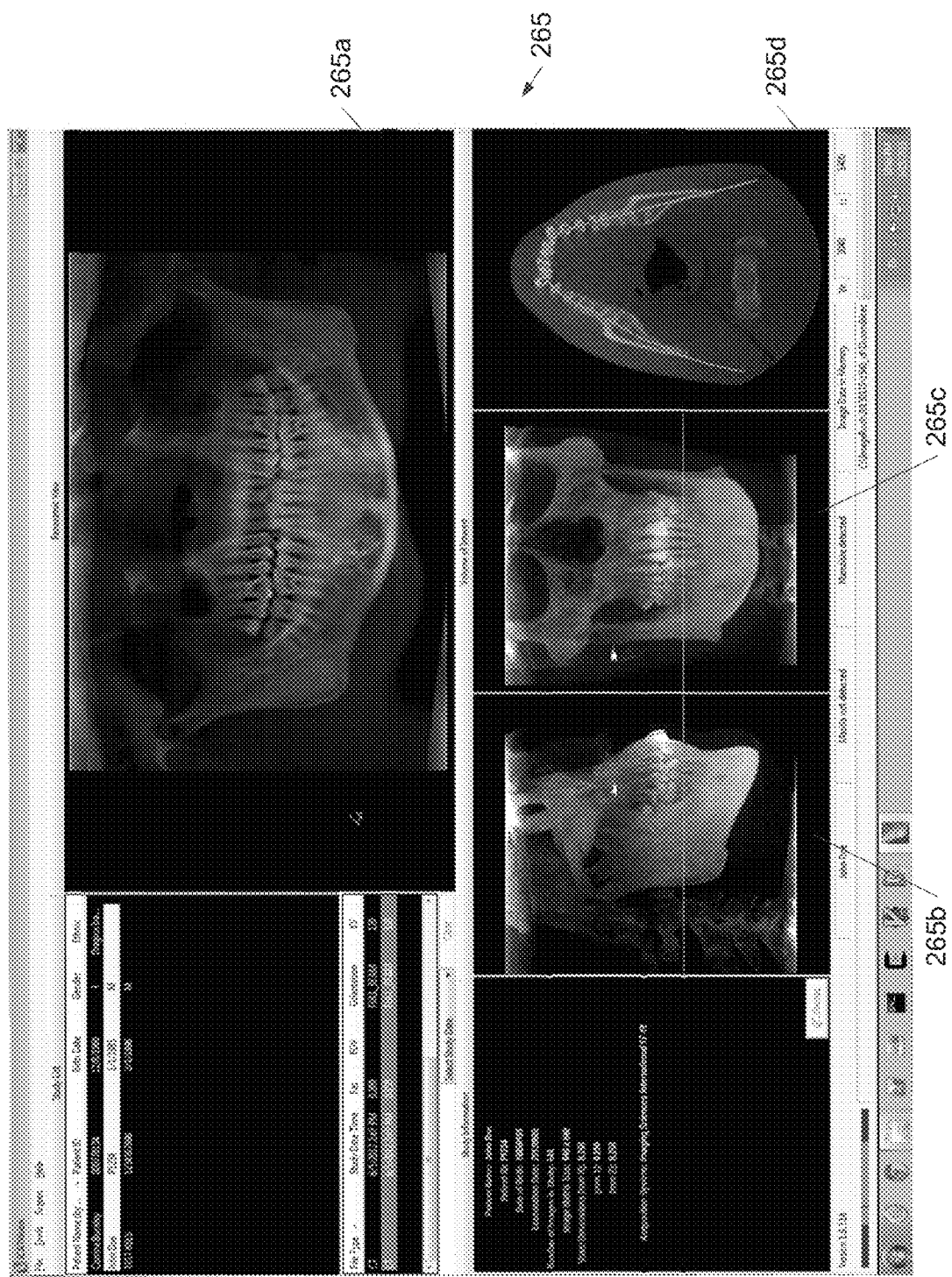
FIG. 9 illustrates an image used by a clinician for patient treatment and planning.

From the projection data, the application 210 generates a first three-dimensional, volumetric data set representing the internal structure of the patient's head or other object being imaged (at step 253). The application 210 is also configured to automatically reconstruct a first image for patient treatment or planning based on the first three-dimensional data set (at step 260). The first image can include a two-dimensional rendering of the three-dimensional data representing the patient's head. The application 210 can be configured to generate the first three-dimensional, volumetric data set and/or the first image based on the image generation settings selected by the user prior to the scan (e.g., scan protocol and/or scan type). For example, the first image typically, but not necessarily, has a field-of-view ("FOV") that is substantially the entire patient's head (e.g., approximately chin to forehead or approximately 13 centimeters in height and 16 centimeters in width). The application 210 generates a signal to display the first image 265 on the touchscreen 110B (at step 270), as illustrated in FIG. 9. In some embodiments, the first image 265 can include multiple versions or views of an image, such as a panoramic view 265a, a side view 265b, a front view 265c, and a top view 265d. A clinician uses the first image 265 to inspect the quality and positioning the scan, treat the patient, or plan a treatment for the patient. The application 210 can also transmit the first image 265 to a local image database server, where the first image 265 can be accessed by other clinicians and other workstations.

Figure 10:
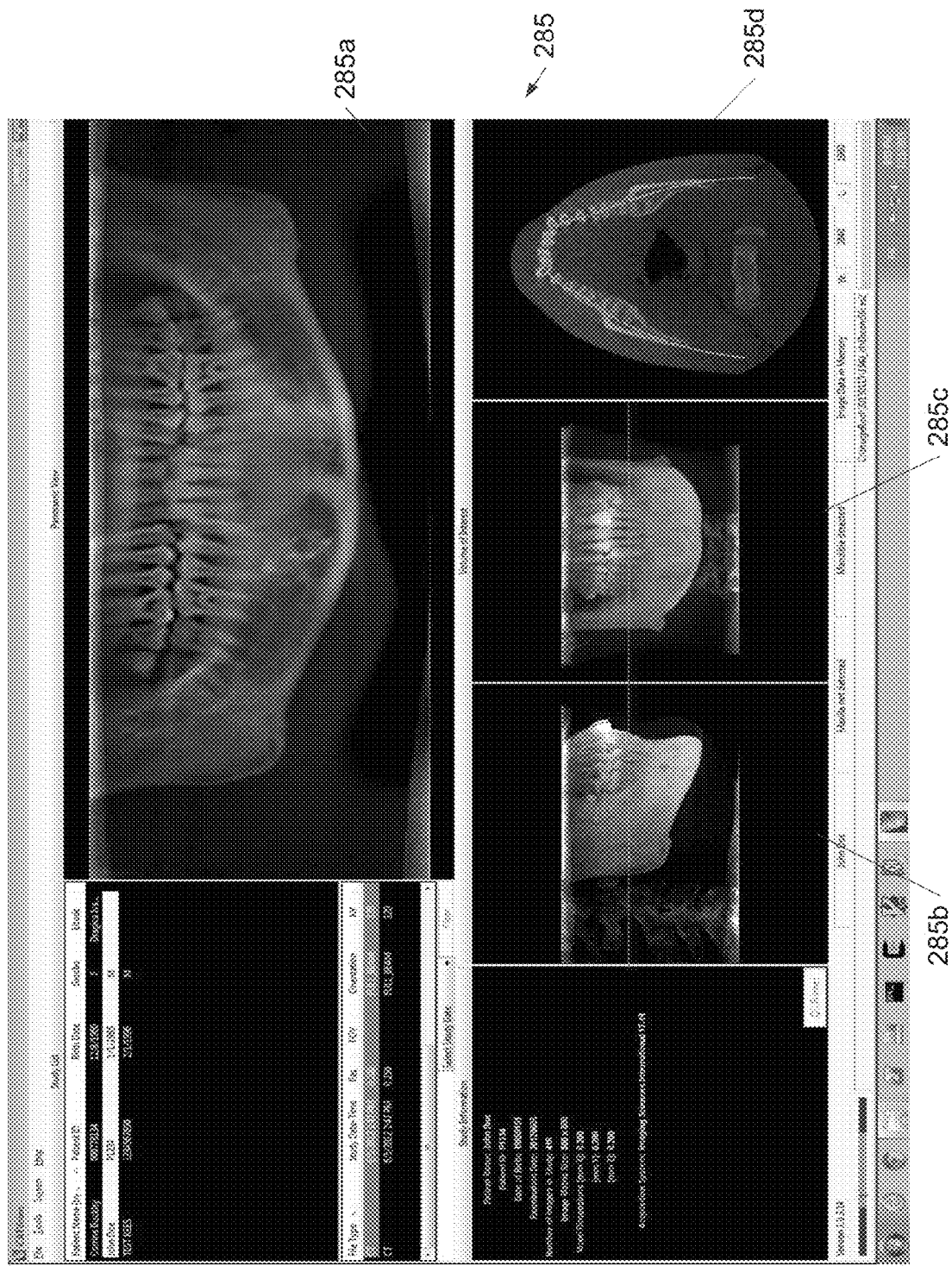
FIG. 10 illustrates an image used by a service provider.

The application 210 also automatically generates a second three-dimensional, volumetric data set for a service provider based on the projection data and the image generation settings (at step 280). The second three-dimensional, volumetric data set typically has a FOV that is smaller than the FOV of the first three-dimensional, volumetric data set in at least one dimension, such as height. For example, as illustrated in FIG. 10, the FOV of the second three-dimensional, volumetric data set can include only the patient's jaw or a portion thereof (e.g., approximately the lower eight centimeters of the full FOV). Optionally, but not necessarily, the application 210 can generate a second image 285 from the second three-dimensional, volumetric data set. In some embodiments, the second image 285 can include multiple versions or views of an image, such as a panoramic view 285a, a side view 285b, a front view 285c, and a top view 285d.

In some embodiments, the second three-dimensional, volumetric data set has a resolution higher (i.e., finer, or having smaller voxels) than the resolution of the first three-dimensional, volumetric data set. For example, the first three-dimensional, volumetric data set can have a resolution of approximately 0.25 millimeter, and the second three-dimensional, volumetric data set can have a resolution of approximately 0.20 millimeter. However, although the second three-dimensional, volumetric data set has a higher resolution, the smaller FOV of the second three-dimensional, volumetric data set allows for the image to be quickly reconstructed without delaying or complicating transmission and processing of the second three-dimensional, volumetric data set or delaying or hindering reconstruction of the first three-dimensional, volumetric data set.

In some embodiments, the application 210 generates the second three-dimensional, volumetric data set in tandem with generating the first three-dimensional, volumetric data set. In other embodiments, the application 210 generates the first three-dimensional, volumetric data set before generating the second three-dimensional, volumetric data set or vice versa. For example, the application 210 can be configured to generate the second three-dimensional, volumetric data set after the first three-dimensional, volumetric data set has been generated and while the first image 265 is displayed on the touchscreen 110B. Accordingly, the application 210 generates the second three-dimensional, volumetric data set without delaying the generation and clinician review of the first three-dimensional, volumetric data set and the first image 265.

As illustrated in FIG. 3, after the second three-dimensional, volumetric data set is created, the application 210 automatically transmits the second three-dimensional, volumetric data set to a service provider, such as a dental appliance manufacturer or an entity that creates customized treatment plans (at step 290). In some embodiments, because the second three-dimensional, volumetric data set is not used by the operator and, thus, the operator has no need to review an image 285 based on the second three-dimensional, volumetric data set, the application 210 transmits the second three-dimensional, volumetric data set to the service provider without generating or displaying to an operator any image based on the second three-dimensional, volumetric data set. As illustrated in FIG. 2, the application 210 transmits the second three-dimensional, volumetric data set to a server 190 operated by a service provider. In some embodiments, the server 190 is configured to automatically process the second three-dimensional, volumetric data set to generate the requested output (e.g., treatment plan, device designs, devices, etc.).

Preferably, but not necessarily, the second FOV has the same horizontal dimensions as the first FOV, but a smaller vertical dimension. For example, the second FOV can be chosen to encompass a patient's jaw and teeth without including features such as the patient's eyes. The second FOV can be chosen in advance using fixed parameters for vertical and horizontal height and position. Alternatively, or in addition, the second FOV can be selected by automatically determining an appropriate vertical height and position based on patient features that appear in the first three-dimensional, volumetric data set For example, in one embodiment, the vertical dimensions and location of the second FOV can be determined by the steps of: generating the first three-dimensional, volumetric data set; automatically detecting the patient's occlusal plane or master arch as described in U.S. Pat. No. 8,325,874, which is incorporated by reference herein; and setting the upper and lower edges of the second FOV at predetermined vertical distances from the occlusal plane or master arch. Optionally, the upper and lower edges of the second FOV can be made equidistant from the occlusal plane or master arch In addition, the vertical dimensions and location of the second FOV can be determined by the steps of: detecting the presence and locations of metal items (e.g., brackets) affixed to the patient's teeth; and setting the upper and lower edges of the second FOV at predetermined vertical distances from the vertical range in which the metal brackets appear. Optionally, the upper and lower edges of the second FOV can be made equidistant from the vertical range in which the metal brackets appear.

It should be understood that although the application 210 is described as being used with a data set representing a scan of a patient's head (e.g., a jaw), the application 210 can be configured to generate three-dimensional, volumetric data sets and images for different purposes based on data acquired from a scan of any piece of anatomy or any object. In addition, other types of scanning procedures can be used to generate the data set. In addition, it should be understood that the application 210 can be configured to generate more than just the first and second three-dimensional, volumetric data sets. For example, the application 210 can be configured to automatically generate multiple three-dimensional, volumetric data sets for processing by a service provider. Also, it should be understood that the characteristics of the first and second three-dimensional, volumetric data set can vary as needed by a clinician and/or a service provider. For example, in some embodiments, the first and second three-dimensional, volumetric data set may have the same FOV and/or the same resolution. In addition, in some embodiments, the functionality of the UI application 210 can be distributed among multiple applications or modules. For example, in some embodiments, separate applications or modules generate the first and second three-dimensional, volumetric data set.

Various features and advantages of the invention are set forth in the following claims.

What is claimed is:

1. A system for generating images, the system comprising:
a processor configured to:
receive image generation settings;
receive projection data generated by a CT scan of an object;
generate a first three-dimensional data set having a first field-of-view of the object, the first three-dimensional data set based on the projection data;
automatically generate a first image based on the three-dimensional data set;
automatically generate a second three-dimensional data set having a second field-of-view of the object smaller than the first field-of-view in at least one dimension, wherein the second three-dimensional data set has a higher resolution than the first three-dimensional data set and the second three-dimensional data set is based on the projection data and the image generation settings; and
transmit the second three-dimensional data set to a service provider over at least one network.

2. The system of claim 1, wherein the object is a head of a patient, and wherein the processor is further configured to determine the second field-of-view by:
automatically detecting an occlusal plane of the patient;
locating an upper edge of the second field-of-view at a first predetermined vertical distance from the occlusal plane; and
locating a lower edge of the second field-of-view at a second predetermined vertical distance from the occlusal plane.

3. The system of claim 1, wherein the processor is further configured to determine the second field-of-view by:
automatically detecting a set of at least one metal item within the object;
determining a vertical region containing the set of at least one metal item;
locating an upper edge of the second field-of-view at a first predetermined vertical distance from at least one edge of the vertical region; and
locating a lower edge of the second field-of-view at a second predetermined vertical distance from the at least one edge of the vertical region.

4. The system of claim 1, wherein the processor is further configured to output the first image to a display.

5. The system of claim 4, wherein the processor is configured to automatically generate the second three-dimensional data set while the first image is output to the display.

6. The system of claim 1, wherein the object includes a human head.

7. The system of claim 6, wherein the service provider includes a device manufacturer.

8. The system of claim 7, wherein the device manufacturer includes a dental appliance manufacturer.

9. The system of claim 1, wherein the first field-of-view includes a substantial portion of a head.

10. The system of claim 9, wherein the second field-of-view includes a jaw and teeth included in the head.

11. A method of generating images, the method comprising:
   receiving, at a processor, image generation settings from an operator;
   initiating, by the processor, a scan of an object with a CT imaging apparatus based on the image generation settings;
   receiving, by the processor, projection data from the CT imaging apparatus acquired during the scan;
   generating, by the processor, a first three-dimensional data set having a first field-of- view, the first three-dimensional data set based on the projection data;
   automatically, by the processor, generating a first image of the object based on the first three-dimensional data set;
   generating a signal to display the first image to the operator;
   automatically, at the processor, generating a second three-dimensional data set having a second field-of-view smaller than the first field-of-view in at least one dimension, wherein the second three-dimensional data set has a higher resolution than the first three-dimensional data set and the second three-dimensional data is based on the projection data and the image generation settings; and
   transmitting the second three-dimensional data set to a device manufacturer over at least one network.

12. The method of claim 11, wherein the object is a head of a patient, and further comprising determining the second field-of-view by:
   automatically detecting an occlusal plane of the patient;
   locating an upper edge of the second field-of-view at a first predetermined vertical distance from the occlusal plane; and
   locating a lower edge of the second field-of-view at a second predetermined vertical distance from the occlusal plane.

13. The method of claim 11, further comprising determining the second field-of-view by:
   automatically detecting a set of at least one metal item within the object;
   determining a vertical region containing the set of at least one metal item;
   locating an upper edge of the second field-of-view at a first predetermined vertical distance from at least one edge of the vertical region; and
   locating a lower edge of the second field-of-view at a second predetermined vertical distance from the at least one edge of the vertical region.

14. The method of claim 11, wherein generating the second three-dimensional data set includes automatically generating the second three-dimensional data set while the first image is displayed to the operator.

15. The method of claim 11, wherein receiving the projection data includes receiving data based on a scan of a human head.

16. The method of claim 15, wherein transmitting the second three-dimensional data set to the device manufacturer includes transmitting the second three-dimensional data set to a dental appliance manufacturer.

17. The method of claim 11, wherein the first field-of-view includes a substantial portion of a head.

18. The method of claim 17, wherein the second field-of-view includes a jaw and teeth of the head.

19. A system for generating images, the system comprising:
   an imaging apparatus configured to scan an object and generate projection data; and
   a processor configured to
   receive image generation settings,
   initiate a scan of the object with the imaging apparatus based on the image generation settings,
   receive projection data from the imaging apparatus generated during the scan,
   generate a first three-dimensional data set having a first field-of-view of the object, the first three-dimensional data set based on the projection data,
   automatically generate, based on the first three-dimensional data set, a first image, generate a signal to display the first image to an operator,
   while the first image is displayed to the operator, automatically generate a second three-dimensional data set having a second field-of-view of the object smaller than the first field-of-view in at least one dimension, wherein the second three-dimensional data set has a higher resolution than the first three-dimensional data set and the second three-dimensional data set is based on the projection data and the image generation settings, and
   automatically transmit the second three-dimensional data set to a remote server operated by a dental appliance manufacturer over at least one network, the remote server configured to automatically process the second three-dimensional data set to generate a design or a treatment plan for at least one dental appliance.

* * * * *